United States Patent [19]

Slemon

[11] Patent Number: 4,937,292
[45] Date of Patent: Jun. 26, 1990

[54] PHOTOSENSITIZER

[75] Inventor: Clarke E. Slemon, Willowdale, Canada

[73] Assignee: Solavchem Enterprises Inc., Canada

[21] Appl. No.: 71,495

[22] Filed: Jul. 9, 1987

[30] Foreign Application Priority Data

Jul. 9, 1986 [CA] Canada .................................. 513436

[51] Int. Cl.$^5$ ........................... C08F 2/50; C08F 8/00; C07C 172/00; B01J 31/06
[52] U.S. Cl. .................................. 525/326.8; 522/35; 522/68; 525/102; 525/156; 525/161; 525/279; 525/327.2; 525/330.5; 525/330.6; 525/359.3; 525/379; 526/284; 204/157.67
[58] Field of Search ..... 522/35, DIG. 904, DIG. 905, 522/68; 525/156, 161, 326.8, 327.2, 330.5, 330.6, 379, 102; 204/157.67; 526/284

[56] References Cited

U.S. PATENT DOCUMENTS

| | | | |
|---|---|---|---|
| 3,926,641 | 12/1975 | Rosen | 522/35 |
| 4,052,280 | 10/1977 | McGinnis | 522/35 |
| 4,089,815 | 5/1978 | Reiter et al. | 522/35 |

Primary Examiner—C. Warren Ivy
Assistant Examiner—T. McDonald, Jr.
Attorney, Agent, or Firm—Mason, Fenwick & Lawrence

[57] ABSTRACT

Photochemical conversion of tachysterols to previtamins is conducted in the presence of a polymeric photosensitizer which has the appropriate chromophore groups, e.g. anthracene groups, attached to a medium or high molecular weight, substantially uncrosslinked polymer backbone. The polymeric photosensitizer is soluble in solvents normally used for conducting the photochemical reaction (diethyl ether, dioxane, THF, t.butyl methyl ether) but insoluble in lower alcohols and hydrocarbons, so that it may be readily and simply recovered from the product mixture by use of such non-solvents.

16 Claims, No Drawings

PHOTOSENSITIZER

FIELD OF THE INVENTION

This invention relates to photochemical sensitizing materials, processes for preparing photosensitizing materials and photochemical processes which involve the use of photosensitizers.

BACKGROUND

In the synthesis of vitamin $D_2$ and vitamin $D_3$, it is common to use photochemical preparation processes. Thus, vitamin $D_3$ is prepared commercially by photolysis of 7-dehydrocholesterol to form pre-vitamin $D_3$ ($P_3$) which is subsequently heated to form vitamin $D_3$. The first stage of photolysis can however form by-products such as lumisterol ($L_3$) and tachysterol ($T_3$), from which vitamin $D_3$ cannot be formed directly. Accordingly, such photolysis processes should minimize the formation of $L_3$ and $T_3$, or alternatively seek to convert the $L_3$ and $T_3$ formed back to $P_3$, in order to maximize the yield of $P_3$ and subsequently of vitamin $D_3$.

PRIOR ART

U.S. patent application Ser. No. 801,853 Stevens, filed Nov. 26, 1985, discloses a process for the photochemical production of vitamin $D_3$ from tachysterol $T_3$ using anthracene as a photosensitizer. Other publications have described the use of other sensitizers for this conversion, e.g. florenone (S. C. Eyley and D. H. Williams, Chem Comm. 858, 1975) and other materials (Marlene Denny and R. S. H. Liu, Nouveau J. de Chemie 2,637,1978). Whilst the use of these sensitizers does indeed lead to significant improvements in the $P_3/T_3$ ratio, there are, on occasions, difficulties in separating the sensitizer from the final product. Because the product is intended for inclusion in food and feed products, it is important to remove most, or essentially all, of the sensitizer from the vitamin gum mixture. It is also important that this separation should be inexpensive, and capable of operation on a large scale.

SUMMARY OF THE INVENTION

It has now been found that radicals of simple sensitizers which catalyze the conversion of $T_3$ to $P_3$ in high yield can be chemically attached to certain substantially uncrosslinked polymeric materials in such fashion that the chromophores retain their photosensitizing characteristics, while the resultant polymeric materials have substantially different solubility characteristics from the vitamin product mixture resulting from their use. Accordingly, by use of the present invention, not only is an efficient, high yield photochemical process for vitamin D manufacture obtained, but also product separation from photosensitizer residues is rendered simple, effective and inexpensive.

By the term "simple sensitizer" as used herein is meant a non-polymeric photocatalyst, such as anthracene or an anthracene compound By the term "chromophore" as used herein is meant the unsaturated, light absorbing molecular substructure of the sensitizer.

The polymeric photosensitizing materials of the present invention consist essentially of a medium to high molecular weight, essentially uncrosslinked, polymer backbone with a chromophore group attached thereto in such a way that the photosensitizing properties of the group are left substantially unchanged. The polymer is predominantly derived from a monomer or comonomers which do not strongly absorb the light wavelengths used to excite the chromophore. The term "sensitizer radical" as used herein refers to the chromophore with its attached groups but without its functionality for attachment to the backbone polymer. The term "sensitizer sub-unit" as used herein refers to a small radical or molecule containing the sensitizer radical with its functionality for chemical attachment. Appropriate functionalities for these latter attachments are, for example, a formyl group (—CHO), a hydroxymethylene ($CH_2OH$), a halomethylene ($CH_2X$), a methylene carboxy (—$CH_2COOH$), a methylene amino (—$CH_2NH_2$), an acetyl (—$COCH_3$) or a (—$COCF_3$).

IN THE DESCRIPTION OF THE PREFERRED EMBODIMENTS

In one protocol of polymer assembly according to the invention, the sensitizer radical can be built into special monomers which also contain a polymerizable functionality These special monomers may be incorporated into the polymerization mixture with the predominant monomer or comonomers in such a concentration that the resultant polymer product will have the desired optical density of chromophores. In a second protocol, the photosensitizer radical may be grafted onto the polymeric material by reaction between the preformed polymer and sensitizer sub-units. The reaction of the sensitizer sub-unit is usually but not necessarily with the functionality of the basic monomer or comonomer units. In a third protocol, a special monomeric material containing a polymerizable group and a protected functional group can be copolymerized with the predominant monomer or monomers; this special monomer providing units in the polymer which after the protecting moiety is removed (i.e., deprotected), the units can subsequently covalently link sensitizer sub-units to the polymeric material. The units so provided in the polymer are chosen so as to have appropriate reactable groups with those chosen as the functionalities of the sensitizer subunit. For example, if aldehyde is chosen as the functionality of the sensitizer sub-unit, a diol group or a group easily convertible to diol can be chosen for incorporation into the polymer from the special monomer unit The sensitizer sub-unit can also be linked to the polymer chain indirectly through what is known to those skilled in the art as a spacer arm. Spacer arms particularly appropriate to this invention are ethyleneoxy (—$CH_2$—$CH_2$—O—)$_n$ or propyleneoxy (—$CH_2$—$CHCH_3$—O—) chains since they complement the desired solubility properties and are simple to incorporate. Also particularly appropriate is HO—($CH_2$)$_n$—$C_6H_4$OH group, since it can easily be sequentially attached to the sensitizer radical and the polymer chain.

In a preferred embodiment of this invention, the special monomer unit in this third alternative is of such a character, that the covalently bound sensitizer radical can be subsequently removed from the polymer backbone and replaced using by new sub-units. Thus, if the sensitizer radicals undergo photochemical side reactions, or otherwise degrade during use, they can be removed and replaced so as completely, or partially, to restore the activity of the photocatalyst without replacing the entire polymeric material.

An essential characteristic of the polymeric catalysts falling within the scope of this invention is that they are soluble in at least one of the solvents normally chosen for the photochemical synthesis of Vitamin D, herein called Group S solvents and exemplified by lower acyclic and cyclic alkyl ethers and polyethers, and particularly, diethyl ether, t-butylmethylether, tetrohydrofuran and dioxane, but they are insoluble in a different group of solvents, herein called Group I and exemplified by saturated hydrocarbons and lower alcohols.

Polymeric catalysts which fall within the scope of this invention can thus be identified and characterized by the solubility characteristics of polymers formed from their predominant monomer or comonomers. If the predominant monomer, or the comonomers in appropriate ratios, produce a material that is soluble in at least one of the Group S solvents and insoluble in at least one of the Group I solvents, then that polymeric material, when modified to contain the sensitizer radicals, and when demonstrated to catalyze the isomerization, falls within the scope of this invention.

Monomers appropriate for preparing polymeric catalysts of this invention include:

butyl acrylate, propyl acrylate, pentyl acrylate, hexyl acrylate, heptyl acrylate, octyl acrylate, 2-ethylhexyl acrylate, propyl methacrylate, butyl methacrylate, vinyl butyrate, vinyl pentanoate, vinylhexanoate, vinylethyl hexanoate, ethyl vinyl ether, propyl vinyl ether, butyl vinyl ether, allylethyl ether, allylpropyl ether, allylbutylether, allylpropionate, allyacetate, allylbutyrate, hydroxyethyl acrylate, 2-hydroxypropyl acrylate, glyoerinmonoacrylate, allyl glyceride, allyl glycol, ethoxyethylacrylate, ethoxyethylmethacrylate, N-butylacrylamide, N-hexylacrylamide, N-cyclohexylacrylamide, N,N-hydroxyethylacrylamide, hydroxyethylmethacrylate, hydroxyethylethacrylate, 2-ethylbutylmethacrylate, butoxyethylene, isobutoxyethylene, t-butoxyethylene, dimethylfulvene.

indene, oxymethylphenylsilylene, butadiene, isoprene, 2-chlorobutadiene, 2-t-butyl-1, 3-butadiene, 2-chloromethylbutadiene, propylene, butylene, cyclopentylethylene, or cyclohexylethylene.

Cellulose may also be used as the base polymer to which the sensitizer radical may be attached.

Sensitizer radicals in this invention are those derived from simple sensitizers which have a triplet energy within the range 35-47 kcal/mole and triplet quantum yields greater than zero, such as anthracene (42.0-42.7), phenazine (44), eosin (42.6), thiobenzophenone (40-43), 9,10-dichloroanthracene (40.4), 3,4-benzopyrene (42), perylene (35.1), trans-1,3,5-hexatriene (47.0), 1-chloroanthracene (42.1), 1,5-dichloroanthracene (41.7), 1,10-dichloroanthracene (40.4), 1,5,10-trichloroanthracene (39.5), 1,4,5, 8-tetrachloroanthraoene (40.5), 9,10-dibromoanthraoene (40.2), 9-methylanthracene (41.4), 9-nitroanthracene (41.8), 1-azaanthracene (43.1), 2-azaanthracene (42.5), acridine (45.3), diphenylbutadiene (42.0), 3,4,8,9-dibenzopyrene (40.3), 7,12-dimethylbenzanthracene, 1,12-benzoperylene and trans-1,2-benzanthracene.

Preferred are sensitizer radicals which are carbocyclic or heterocyclic aromatics, for example heterocyclic aromatics containing ring nitrogen heteroatoms.

Most preferred are sensitizer radicals having an anthracene, aza-anthracene or polyaza-anthracene nucleus which is unsubstituted, substituted or polysubstituted at any positions with halogens, except iodine, and/or with one or more lower alkyl or cycloalkyl radicals, and/or with other phenyl substituents.

The photosensitizer radical should be incorporated into the polymer in such a quantity as to give the polymer material a high absorbance to mass ratio relative to the substrate but not in so large a quantity as to cause side reactions of the sensitizer radicals to dominate the chemistry, and particularly, not in so large a quantity as to change the desired solubility-insolubility behaviour of the polymeric catalyst.

The invention should not be construed as limited to any specific method or methods or incorporating substantial quantities of sensitizer radicals into the polymer material. Preferred such methods are those which enable the practice of this invention using relatively small quantities of polymer catalyst along with relatively large quantities of the Vitamin D producing materials, and which also allow flexibility in controlling the final level of absorbance of the polymeric photocatalyst.

Thus the present invention provides polymeric photocatalysts for use in catalysing photochemical conversion of tachysterols to previtamins in solution, said photocatalysts comprising sensitizer radicals with appropriate photophysical properties for catalysing the reaction, bonded covalently to a medium to high molecular weight substantially non-crosslinked polymeric backbone, said polymeric photocatalysts being soluble in a first solvent medium used for conducting the photochemical reaction, and in which the previtamin reaction product is soluble, but insoluble in at least one other, second solvent in which the previtamin reaction product is soluble.

Accordingly, the present invention provides, in a preferred embodiment, polymeric materials containing sensitizer radicals chemically bound thereto, said sensitizer radicals being active to sensitize the photochemical preparation of pre-vitamin $D_2$ or pre-vitamin $D_3$, said polymeric material containing monomer units of the general structure

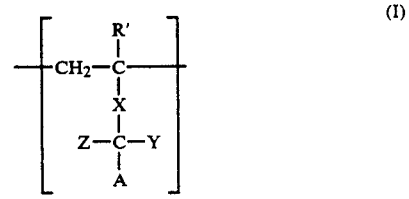

(I)

wherein

Y and Z are independently selected from hydrogen, lower cycloalkyl or one or both of Y and Z, together with group X, form a heterocyclic group containing one or more hetero atoms selected from oxygen, nitrogen and sulphur;

R' represents hydrogen, lower alkyl, carboxylic acid ester, carboxylic acid carboxylic acid amide or lower alkoxy:

X represents a covalent bond or a covalent chemical bridge consisting essentially of covalently linked lower alkylene groups, phenyl groups, substituted phenyl groups, oxygen atoms, sulphur atoms, or nitrogen atoms, alone or linked as ester, amide, carbonate carbamate or ureido linkages or combinations of said groups and linkages;

and A is a sensitizer radical derived from a simple sensitizer having a triplet energy within the approximate range 35–47 kcal/mole, and a triplet quantum yield greater than zero.

In a preferred embodiment of the invention, an anthracene radical is linked to the polymer chain side group through one of its carbons, and is substituted at its 9- and 10-positions in such a way as to diminish the tendency of the anthracene radical to dimerize, or otherwise undergo side reactions which would reduce its photocatalytic activity. In one preferred embodiment, the anthracene radical joins to the polymer through its 9-position, and is substituted at its 10-position with a lower alkyl group R, so that the photosensitive sub-unit corresponds to the general formula

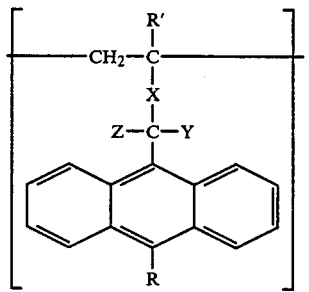
(II)

Groups X, Y and Z in general formula I and II can be chosen from a wide range of chemical groups, provided that certain basic criteria are followed. They must not interfere with the photochemistry of the chromophore moiety. Thus the chosen groups must leave intact and not extend the conjugated structure of the anthracene moiety. Also, in the case of compounds containing structure (II), they must be chosen so that the carbon atom linked to the anthracene moiety (the α-carbon) is tetrahedral, i.e. no double-bonding to the α-carbon can be permitted unless that carbon is part of a phenyl ring.

In one embodiment of the invention, group Y in formula II represents a lower alkyl group, for example methyl, or hydrogen, and groups X and Z together form a heterocyclic group linked to the polymer through an alkylene ester amide etc. group. An example of such a group is a cyclic ketal, to provide a compound of formula II, of structure

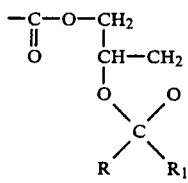

where R is 10-methyl-9-anthracyl and $R_1$ is hydrogen. Such a compound can be prepared by reacting a polymer containing the above-described cyclic ketal under mild conditions with 9-aldehydo-10-methyl anthracene.

A further example of a suitable such heterocyclic group is a cyclic hemi thioketal, of structure

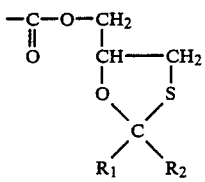

or

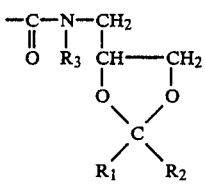

where $R_1$, $R_2$ and $R_3$ represent lower alkyl groups. This will similarly react with the anthracene aldehyde derivative to produce the desired product.

The most convenient way of preparing the polymeric photosensitizer of the present invention is by reaction of a polymer bearing an appropriate reactive side group with 9-aldehydo anthracene to give a polymer bearing photoresponsive groups of general formula II. Specific alternative anthracene compounds which can be used include 9-aldehydo-10-chloroanthracene and 2-aldehydo-9,10-dichloroanthracene. Accordingly, preferred compounds of the invention are those derived from polymers bearing such aldehyde-reactive groups. Specific examples of such side groups include the cyclic ketals and cyclic thioketals as described above. Other suitable such side groups are:

1, 2 and 1,3-diols
1, 2 and 1,3-aminoalcohols;
1, 2-dithiols
1, 2-aminothiols;
orthoester;

Most preferably, these polymer side groups are such that their linkage to the photosensitizer moiety is reversible to restore the original side group, for removal and subsequent replenishment of the photosensitive groups on the polymer.

The form of covalent chemical bridge between the aldehyde-reactive group and the main polymer backbone is not critical, provided of course that it does not interfere with the photochemical characteristics of the anthracene group and provided that it does not detract from the desired solubility properties of the polymer. It can be a straight or branched chain alkylene linkage, a cycloalkylene linkage, a phenylene linkage an ester linkage an amide linkage an ether linkage a urethane linkage etc., or a combination of such links. It is preferred that the linkage to the polymer chain be chemically more stable than the bond between the aldehyde-reactive side group and the anthracene radicals, so that degraded or dimerized anthracene radicals can be chemically removed and replaced without at the same time stripping the aldehyde reactive group from the polymer backbone.

Thus from another aspect, the present invention provides polymeric materials containing photosensitive anthracene radicals and comprising an ether-soluble but alcohol or hydrocarbon insoluble polymeric material, said anthracene radicals being linked to the polymer backbone through a tetrahedral carbon atom at a position α to the anthracene moiety and a covalently linked chemical bridging group extending from the α-carbon to the polymer chain, said α-carbon-chemical bridging group resulting from the reaction of an aldehyde group on the anthracene with an aldehyde reactable group on a side group linked to the polymer backbone.

The precise nature of the polymer which is used in the present invention is not critical, provided that it has the specified side groups to which the anthracene moieties are attached, in sufficient quantity, and provided that it meets the aforementioned solubility characteristics, i.e. soluble in solvents used in the photolysis process (normally ethers) and insolubility in lower alcohols or hydrocarbons used to work up the photolysate. It may be a homopolymer or copolymer of two or more monomers. Suitable functional side groups, for linking to the anthracene radicals, may be included in the monomer or monomers prior to polymerization, or the polymer may be modified subsequent to polymerization to put such side groups in place.

It is preferred to prepare a polymer for the present invention from two or more monomers, one of which contains a suitable functional group which will not participate in the polymerization reaction, but which will provide all of the required functional side groups in the resultant copolymer. In this way, better control of the amount of anthracene moieties to be linked to the polymer material can be exercised.

An example of a special monomer unit specifically suitable for this purpose is that prepared by reaction of acryloyl chloride and solketal, thus:

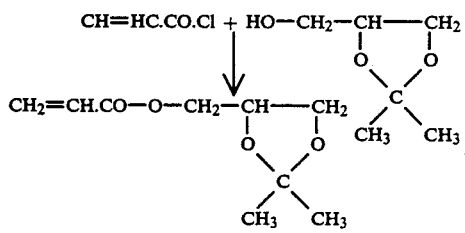

This special monomer unit is readily copolymerizable with a variety of comonomers, e.g. acrylic and methacrylic acids, esters, nitriles etc., to form copolymers therewith of medium or high molecular weight which are soluble in ether solvents but substantially insoluble in alcohols. Normal polymerization systems known and used for the common comonomers can be adopted for this copolymerization.

The ketal structure of the side groups incorporated into the copolymer by use of this monomer reacts readily and easily with aldehyde-substituted anthracene, as follows:

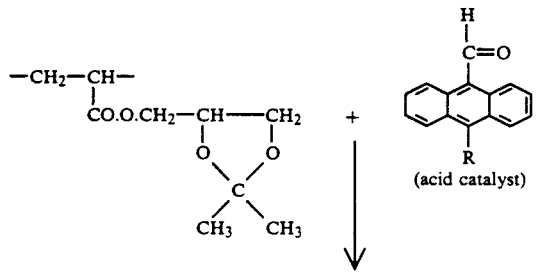

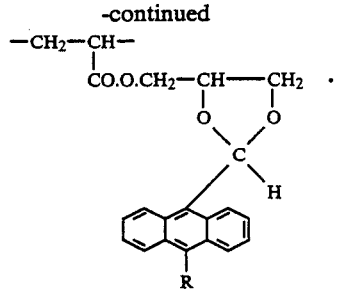

The link holding the anthracene moiety to the polymer is reversible, as previously discussed, because the ketal group can be preferentially cleaved to separate the sensitizer sub-unit from the remainder of the chemical covalent linkage to the polymer backbone Accordingly, if and when necessary, the anthracene radicals can be removed and replaced, to "recharge" the polymer and improve its photosensitivity, without removing the functional side groups from the polymer backbone. Alternatively, some new sensitizer sub-units can be reacted with previously unreacted special monomer units in the polymer.

The polymeric photosensitizer of the present invention is used in vitamin D preparation in substantially the same way as the use of anthracene described in aforementioned U.S. Patent Application Serial No. 801,853. In the process, a solution containing a mixture of pre-vitamin D, tachysterol, lumisterol and 7-dehydrocholesterol, as obtained by the first stage photolysis of 7-dehydrocholesterol, may be mixed with a small catalytic quantity of polymeric photosensitizer and irradiated at a wavelength where essentially only the sensitizer absorbs. The quasi-photostationery state produced is very rich in the $P_3$ isomer which is the precursor of vitamin D:. The ether solvent is removed down to a small volume, and the residue is then added to methanol, ethanol, hexane, isooctane, or other non-solvent for the polymer, which causes the polymer to precipitate as a viscous oil or filterable solid. The photo product mixture remains dissolved in the alcohol or other non-solvent for the polymer. The polymer is separated either by filtration, or by centrifugation/decantation from the solution. The solution is then treated in the usual way to produce vitamin D.

DETAILED DESCRIPTION OF SPECIFIC EMBODIMENTS

The invention is further illustrated by the following specific examples.

EXAMPLE 1

Monomer Synthesis 204.5g 98% acryloyl chloride was dissolved in 500 ml dichloromethane. This was added dropwise, over a period of 3.5 h. to a solution of 298.5g 98% solketal and 187.5g pyridine in the 500 ml dichloromethane. After 2 h, a water bath (15° C) was used to remove heat produced by the reaction After addition of the acryloyl chloride solution was complete, the mixture was stirred at room temperature for 0.5h. It was then heated and stirred, until dichloromethane had been refluxing for 1.5h.

The solution was then extracted with 1 L of 10 wt. % aqueous sodium bicarbonate solution. The phases were then separated in portions over a 2 h period. The dichloromethane phase was dried with magnesium sulphate overnight. It was then gravity filtered and the dichloromethane was removed on the rotary evaporator. 166 g of an orange oil was collected.

The oil was then distilled under water aspirator vacuum. A clear fraction was removed. A second fraction (100 g), a yellowish oil, was removed, leaving behind a viscous orange residue. (An infrared spectrum of the second fraction was taken, as well as an NMR.)

EXAMPLE 2

Copolymer Synthesis 9.6g of monomer prepared according to Example 1, 15.4 g distilled butyl acrylate, 500 mL toluene and 0.075 g AIBN (recrystallized from methanol and stored in a freezer) were combined in an unstirred flask (in that order). The flask was then evacuated using a water aspirator and then charged with a light positive pressure of nitrogen. This degassing procedure was repeated 5 times (6 times total leaving a positive pressure of nitrogen over the degassed solution). It was then heated to 60° C for 12 h.

The solution was then concentrated to 50 ml on the rotary evaporator. This solution was added dropwise to 1 L vigorously stirred methanol. It was allowed to settle for 15 min., then the methanol was decanted. 100 ml pure methanol was then added to wash the polymer. It was allowed 5 min. to settle, then the methanol was decanted. 7.3 g of polymer was collected after removal of solvents on the vacuum apparatus.

EXAMPLE 3

9-Anthraldehyde Bonding to Copolymer 7.3 g of polymer was dissolved in 250 mL reagent grade dioxane at 40° C. 3.5 g anthraldehyde (90% pure, remainder anthracene) was then added in the solid form. 0.0611 g toluene sulphonic acid was then added. Dioxane was refluxed vigorously with the reflux condenser heated to 60° C with a temperature controlled water bath. After 0.5 h, the temperature of the condenser was increased to 70° C, where it was maintained overnight. The dioxane solution was stirred vigorously throughout.

The dioxane solution was concentrated to 50 mL on the rotary evaporator. This was added dropwise to 1 L vigorously stirred methanol. The methanol was left to settle for 15 min., then decanted. The polymer was washed with 100 mL methanol, which was allowed to settle for 5 min. then decanted. It was then dissolved in 25 mL dichloromethane. It was precipitated in 500 mL methanol, washed and redissolved in dichloromethane four more times. It was then precipitated twice in 500 mL hexane.

At this point, the ultraviolet spectrum of the polymer was recorded. 188.9 mg polymer were dissolved in methyl-t-butyl ether to make a 25 mL solution. 1 mL of this solution was diluted with MTBE to make a 10 mL solution. The absorbance at 364 nm in a 1 cm pathlength quartz cell of this solution with pure MTBE as a reference was 374. A sample of hexane from the final precipitation was centrifuged and the UV spectrum was taken in a 1 cm quartz cell with MTBE as a reference. The absorbance of the hexane at 364 nm was 0.016, just above the baseline.

EXAMPLE 4

Experimental Procedure 251.6 mg of recrystallized 7-DHC (from acetone) was dissolved in 250.0 ml of methyl t-butyl ether (MTBE) in a 250 ml volumetric flask. The solution was degassed with argon. Then it was irradiated as it passed through a flow cell. The flow cell was made from 5 meters of 1/4 inch OD 2 mm ID Pyrex tubing, wound in a tight coil approximately 6 cm in diameter and 15 cm in length. The irradiating lamp was a low pressure mercurY lamp, namely a 25 cm × 25 cm flat bed BHK model 88-9660-04 lamp, located approximately 5 cm from the flow cell. Irradiation took place at an average intensity of 2.7 m. watts per $cm^2$ (as determined by an OA1 exposure monitor equipped with a 260 mm probe. The flow rate was kept near 10 ml/min. When all of the solution had passed through, the flow was reversed. Two passes were done. Measured average flow rates were 9.9 ml/min. and 11.4 ml/min. for the first and second passes respectively. The solution was then removed and analyzed by HPLC. The solution was stored overnight in the freezer.

The correct concentration of polymer for the 2nd stage was obtained as follows: 0.3786 g of polymer was dissolved in 25.0 ml dichloromethane. 16.5 ml of this solution was reduced to dryness. The polymer residue was dissolved in 200 ml of 1st stage irradiated solution. The UV spectrum was taken of the starting solution, showing $A_{364}=1.172$. This solution was then degassed in the same manner as before, for 20 minutes. Then the solution was passed back and forth quickly through the flow cell described above, at a wavelength of 350–400 mm from the lamp, at a flow rate of about 40 ml/min. Samples were removed for analysis by HPLC, after passes 4 through 10 inclusive. After 10 passes, the solution was removed from the reservoir, and the UV spectrum remeasured. $A_{364}=0.707$ Volume $=132$ ml. The solution was stored overnight in the freezer.

The solution was reduced to dryness by removing the solvent. The residue was dissolved in 15 ml MTBE. This solution was added dropwise into 500 ml vigorously stirred methanol. The polymer precipitated as an oil at the bottom of the flask. The methanol solution was allowed to settle, then a sample was removed and centrifuged for 20 min. The UV spectrum of this methanol was run, showing barely more than baseline absorbance at 364 nm. The methanol layer was analyzed by HPLC, and the $P_3$ concentration was correct. The results are shown in the following Table.

| SAMPLE | SUMMARY OF HPLC RESULTS mg/ml (%) | | | | |
|---|---|---|---|---|---|
| | $P_3$ | $L_3$ | $T_3$ | 7-DHC | Mass Balance |
| Starting Solution | | | | 1.014 | 1.014(100.8) |
| Solution After 1st Stage | .198(19.7) | .022(2.2) | .662(65.8) | .066(6.6) | 0.948(94.2) |
| Solution After Storing Overnight | .197(19.6) | .020(2.0) | .642(63.8) | .050(5.0) | 0.909(90.4) |
| Sample After 5 Passes, 2nd Stage | .681(67.7) | .017(1.7) | .116(11.6) | .044(4.4) | 0.858(85.3) |
| Sample | .733(72.9) | .021(2.1) | .049(4.9) | .050(5.0) | 0.853(84.8) |

-continued

| SUMMARY OF HPLC RESULTS mg/ml (%) | | | | | |
|---|---|---|---|---|---|
| SAMPLE | P₃ | L₃ | T₃ | 7-DHC | Mass Balance |
| After 6 Passes, 2nd Stage Solution | .732(72.8) | .020(2.0) | .02(2.0) | .041(4.1) | 0.822(81.7) |
| After 2nd Stage, Sitting Overnight Methanol Solution (520 ml) | .178 | | | | |

Essentially similar results were obtained when the methanol used as described above to precipitate the polymeric photsensitizer was replaced, in one case with hexane and in another case with iso-octane.

EXAMPLE 5

9-chloromethylanthracene (2.49 g, 11 m moles) dissolved in acetone is added dropwise to a well stirred suspension of butoxycarbonylthiolan-3-one ($CaH_{14}O_3S$, 2.02 g, m moles) and potassium carbonate (5.52 g, 40 m moles) in acetone. The mixture is refluxed until TLC indicates the essential disappearance of starting -keto acid. The mixture is filtered to remove residual potassium carbonate and inorganic salts and the solvent is removed. The mixture is purified from some 0-alkylated product by flash chromatography using as solvent a mixture of hexane-ethyl acetate which gives Rfs of 0.1-0.2 for the silica absorbent being used The 4-butoxycarbonyl-4-D-(9-anthracylmethyl)thiolan-3-one is treated with the biphasic of diethyl ether and 5% aqueous sodium hydroxide at room temperature in the presence of a small amount of benzyltriethylammonium chloride. When TLC shows the essential disappearance of starting material the product is isolated by separating, drying and evaporating the ether phase. The product n-butyl-2-(9-anthrocylmethyl)acrylate is a special monomer unit. It is copolymerizable with, for example, butyl methacrylate, to obtain a photosensitive polymeric catalyst of the invention.

EXAMPLE 6

To a stirred ether solution of 9-anthraoylmethanol (2.08 g, 10 m moles) and disisopropylethylamine (1.29 g, 10 m moles) is added dropwise at 0° C in an ice bath, an ether solution of previously distilled methacryloyl chloride (1.06 g, 12 m moles). The mixture is stirred for 6 hours at ice temperature or until the starting alcohol is no longer prominent by TLC. The cold ether mixture containing insoluble amine hydrochloride is separated by inverted filtration using a small filter stick and the amine hydrochloride is washed with a little cold ether which is similarly removed. The ether is extracted with cold 5% aq. sodium hydroxide and then with cold 5% aq. oxalic acid. Any solid which separates is removed by filtration through celite. The 9-anthracyl methyl methacrylate [31645-35-9] is obtained as a solid. This is a suitable specialty monomer for copolymerizing with butyl methacrylate.

EXAMPLE 7 SPECIALTY MONOMER

In a 100 ml erlenmeyer containing a magnetic stirrer, 9-chloromethyl 10-chloro anthracene (4.31 g, 16.5 m moles) is dissolved in 20 mL of methylene chloride and 4-(2-hydroxyethyl)phenol (2.76 g, 20 m moles) is added as solid to the solution. All the phenol does not dissolve. A 40% aqueous sodium hydroxide solution (5 mL) is added to the mixture and the biphasic mixture is cooled in ice. A small quantity of tetrabutyl ammonium hydrogen sulfate (30 mg) is added to the stirred mixture and the reaction is vigorously stirred for 2 hours and is then allowed to stir overnight at room temperature with the flask closed. The layers are separated and the methylene chloride is washed with a 20 ml portion of 10% aqueous sodium hydroxide. The methylene chloride is then washed with 20 ml of water and dried over magnesium sulfate. Evaporation of the solvent gives about a 70% yield of crude product which can be purified by crystallization from ethanol or by flash chromatography using an ethyl acetatehexane mixture which gives an $R_f$ of 0.1-0.2 with the silica gel being used.

To a stirred solution of 4.0 g of the above $C_{23}H_{19}ClO_2$ sensitizer sub-unit (11.03 m moles) in (80 ml) diethyl ether is added 1.55 g (12 m moles) of diisopropyl ethyl amine and distilled acryloyl chloride (1.27 g, 14 m moles) in 20 ml of ether solution is added dropwise at 0° C over an hour. The mixture is then stirred 6 hours at room temperature. The cold ether solution containing insoluble amine hydrochloride is cooled to -10 to -15° in ice-methanol and filtered by inverted filtration through a filter stick. The solid is washed with more cold ether The ether is first vigorously stirred and then extracted with an equal volume of cold 5% aqueous sodium hydroxide and then extracted with cold 5% aqueous oxalic acid. Any solid which separates is filtered through celite. The ether is dried with $MgSO_4$, filtered and evaporated to a crude product which is purified by low temperature crystallization from hexaneether. The product (2.1 g, 50%) is dried under vacuum at room temperature and used as a special comonomer in polymer synthesis.

EXAMPLE 8

Allyl 2-nitrobenzyl ether (1.93 g, 10 m moles) and allyl n-butyl ether (11.4 g, 100 m moles) are combined in a flask with 400 ml of toluene and 0.10 g of AIBN (recrystallized from methanol and stored in a freezer) the flask is evacuated using a water aspirator and is charged with argon repeatedly (5×) and left with a positive pressure of argon. The solution is heated at 60° C in an oil bath for 12 hours. The solution is concentrated to a small volume (oil must not come out) and is added dropwise to 1.5 litres of rapidly stirred methanol. The supernate solution is removed and the polymer re-dissolved in toluene and re-precipitated in methanol, twice. The solvent is mostly decanted and the residue removed by drying in a vacuum. The purity of the polymer is determined by a constant optical density on reprecipitation The copolymer of allyl butyl ether and allyl 2-nitrobenzyl ether thus obtained is dissolved to make a 1% solution in distilled degassed toluene and is irradiated with a medium pressure mercury lamp immersed in the cooled stirred solution until there is no longer any appreciable change in the UV absorbance. The toluene solution is concentrated to a small volume (no polymer must precipitate) and 9-anthracyl acetyl chloride (5.10 g, 20 m moles) and triethylamine (1.01 g, 10 m moles) is added and stirred for 12 hours at room temperature. The entire mixture is added dropwise to 1.5 litres of methanol containing (1.01 g, 10 m moles) more triethylamine. The precipitated polymer is washed with methanol, redissolved in toluene and reprecipitated repeatedly. The purity is shown by constant optical density for the anthracyl chromophore in the polymer.

EXAMPLE 9

0.4 (10 m moles) of a 60% NaH dispersion in oil is placed in a 200 ml 3-necked r.b. flask with a magnetic stirrer and reflux condenser with 10 ml of dry toluene to remove the oil and the toluene is carefully decanted by pipette. 2.21 g (10 m moles) of 9-anthrocyl methyl methyl amine was added in 20 ml of toluene and refluxed under nitrogen for three hours. A solution of 25.6 g poly-n-butyl acrylate in 100 ml toluene is added and refluxing continued for 48 hours under nitrogen The reaction is quenched by adding 2 ml of butanol. The solution is concentrated to a smaller volume (100 mL) and added drop by drop to 2 L of hexane cooled to 0° C. The polymer separates as the addition proceeds. The polymer is redissolved in toluene and reprecipitated until a constant optical density is obtained.

EXAMPLE 10

The mixed polymer of solketal acrylate and butyl acrylate (18.6 g) was dissolved in a solution of 2.28 g of periodic acid dissolved 200 mL of dry THF. The iodic acid separates out quickly because it is highly insoluble. The solution is decanted and the solid washed with THF. The solution is concentrated on the rotovap to remove formaldehyde and acetone and then mixed with 2.21 g (10 m moles) of anthracyl methyl methyl amine and 0.67 mL of 5N methanolic HCl previously dissolved in the minimum amount of methanol. Methanol is slowly added until cloudiness just appears or 10% of the THF volume is added. 0.42 of sodium cyanoborohydride was dissolved in 8 mL of dry THF and added slowly with stirring to the mixture. The reaction mixture was left for 72 hours. The pH is then lowered to about 4 by adding 5N methanolic HCl and stirred 1 hour. The solution is concentrated to a small volume and added drop by drop to one hundred times the THF volume of methanol, to precipitate the modified polymer. The polymer is dissolved in toluene and reprecipitated in methanol to a constant optical density

EXAMPLE 11

Poly-butylacrylate (17.4 g) is dissolved in 60 mL of dry benzonitrile in a round bottomed flask with magnetic stirrer and a condenser system which can be used to distil solvent or for total relux. The system is completely under an argon atmosphere. 5.7 g of triphenylphosphine is added, and the system heated to reflux, and a small amount of solvent distilled to remove residual traces of water from the reactor system. The mixture is cooled to room temperature and 1.8 g of dry bromine in 30 mL of dry benzonitrile added under argon. The resultant mixture is heated at 180° C under reflux overnight and the solution returned to room temperature 4.5 g of anthracene methanol, which has been thoroughly dried by distillation in toluene (25 mL) was mixed with 3.8 g of diisopropl ethylamine (dried over sodium hydroxide) and 0.1 g of 4-dimethylaminopyridine, and added to the polymer mixture The solution is stirred at room temperature for 12 hours and then heated at 50° C for 12 hours. The polymer solution is concentrated and precipitated into methanol. Dissolution in toluene and precipitation gives, after several repeats, a purified photopolymeric catalyst material.

EXAMPLE 12

6.0 g of poly n-butyl acrylate resin (which had been thoroughly pumped down under vacuum) was dissolved in toluene in a 100 mL round bottom flask, and the toluene distilled to remove water, alcohol and other protic impurities. 50 mL of chloroform was purified by passing it through a column of Activity I Alumina directly into the flask. The flask was equipped with a condenser and flushed with nitrogen 130 microlitres of iodotrimethyl silane was added and the mixture stirred and refluxed under nitrogen for six hours. After the reaction cooled, a drop of mercury was added and the mixture stirred. In a separate 100 mL round bottom flask, 187.4 mg of 9-anthracene methanol was dissolved in 20 mL of dried (ethanol-free) chloroform. Again under nitrogen 100 microlitres of hexamethyl disilazane was added and refluxed with a continuous flow of nitrogen for 6 hours. The second mixture was transferred in the absence of moisture into the first, and the contents were refluxed for 14 hours.

After cooling, some chloroform was removed on the rotovap, leaving a total solution volume of 30 mL. This solution was added dropwise to 300 mL of vigorously stirred methanol. Some polymer precipitated to the bottom of the beaker. The methanol was decanted off, and the polymer was dissolved up in 20 mL dichloromethane. This solution was added dropwise to 300 mL vigorously stirred methanol. The methanol was decanted off, leaving precipitated polymer.

A solution of 261.4 mg of this polymer dissolved in 25 ml methyl t-butyl ether gave an absorbance curve characteristic of anthracene, with an absorbance maximum at 363 nm of 0.1.

EXAMPLE 13

Tube Reaction of Polybutylacrylate with Anthracenemethylamine

Into each of two tubes, there was loaded 3.5 g of 40% polybutyl acrylate solution in toluene, 500 mg anthracene methylamine dissolved in about 2 ml dimethylsulphoxide, and 15 microlitres acetic acid. The tubes were flame sealed, while frozen under vaccum. They were put into an oil bath, and heated at 200–250° C for 15 hours.

The tubes were then opened, and the dark contents were added dropwise to 150 ml stirred methanol to precipitate the polymer. The resulting product was a bright red solution and a light brown solid. This solid was not completely soluble in ether, and so as much of it as could be was dissolved in about 100 ml ether, and the insoluble portion filtered off, and washed with more ether. The total ether solution was almost red. This was reduced to dryness, then about 5 ml of ether was added to make a red solution. A few drops of methanol were added to help precipitation, then the solution was added dropwise into 150 ml methanol. THe precipitated polymer was collected by decanting the methanol. The polymer was precipitated twice more in this manner, each time the decanted methanol became lighter. The polymer always seemed to retain a light brown colour.

The fourth methanol layer was decanted off, and the remaining polymer was dissolved in ether, then precipitated a fifth time. The loading was 0.12% anthracyl groups on the polymeric material.

I claim:

1. Polymeric photocatalysts useful in catalysing photochemical conversions of tachysterols to previtamins in solution, said photocatalysts comprising sensitizer radicals with appropriate photophysical properties for catalysing the reaction, bonded covalently to a medium to high molecular weight substantially non-crosslinked polymeric backbone, said polymeric photocatalyst being soluble in a first solvent medium used for conducting the photochemical reaction, and in which the previtamin reaction product is soluble, but insoluble in at least one other, second solvent in which the previtamin reaction product is soluble, said first solvent comprising at least one of the group comprising diethyl ether, tbutyl methyl ether, dioxane and tetrahydrofuran, and said second solvent comprising at least one hydrocarbon or lower alcohol;

wherein said polymeric backbone is derived predominantly or exclusively from one or more of the following monomers: butyl acrylate, propyl acrylate, pentyl acrylate, hexyl acrylate, heptyl acrylate, octyl acrylate, 2-ethylhexyl acrylate, propyl methacrylate, butyl methacrylate, vinyl butyrate, vinyl pentanoate, vinylhexanoate, vinylethyl hexanoate, ethyl vinyl ether, propyl vinyl ether, butyl vinyl ether, allylethyl ether, allylpropyl ether, allylbutylether, allylpropionate, allylacetate, allylbutyrate, hydroxyethyl acrylate, 2-hydroxypropyl acrylate, glycerinomonoacrylate, allyl glyceride, allyl glycol, ethoxyethylacrylate, ethoxyethylmethacrylate, N-butylacrylamide, N-hexylacrylamide, N-cyclohexylacrylamide, N,N-hydroxyethylacrylamide, hydroxyethylmethacrylate, hydroxyethylethacrylate, 2-ethylbutylmethacrylate, butoxyethylene, isobutoxyethylene, t-butoxyethylene, indene, oxymethylphenylsilylene, propylene, butylene, cyclopentylethylene or cyclohexylethylene.

2. The polymeric photocatalysts of claim 1, wherein the sensitizer radicals have triplet energies between 35 and 47 kcal/mole and triplet quantum yields greater than zero.

3. The polymeric photocatalysts of claim 1, wherein the sensitizer radicals are those derived from simple sensitizers selected from anthracene, phenazine, eosin, thiobenzophenone, 9,10-dichloroanthracene, 3,4-benzopyrene, perylene, 1-chloroanthracene, 1,5-dichloroanthracene, 1,10-dichloroanthracene, 1,5,10-trichloroanthracene, 1,4,5,8-tetrachloroanthracene, 9,10-dibromoanthracene, 9-methylanthracene, 9-nitroanthracene, 1-azaanthracene, 2-azaanthracene, acridine, 3,4,8,9-dibenzopyrene, 1,12-dimethylbenzanthracene, 1,12-benzoperylene and trans-1,2-benzanthracene.

4. The polymeric photocatalysts of claim 2, wherein the sensitizer radicals are fused carbocycles or heterocycles of the anthracene skeleton, containing one or more alkyl, aryl substituents or halogen substituents.

5. The polymeric photocatalyst of claim 1, wherein the sensitizer radicals are derived from anthracene.

6. Polymeric materials containing photosensitive anthracene radicals chemically bound thereto, said photosensitive groups being active to sensitize the photochemical preparation of pre-vitamin $D_2$ or pre-vitamin $D_3$, and corresponding to the general formula

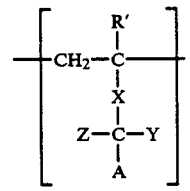

wherein

Y and Z are independently selected from hydrogen, halogen, lower alkyl, cycloalkyl or one or both of Y and Z, together with group X, form an alicyclic group, or a heterocyclic group containing one or more hetero atoms selected from oxygen, nitrogen and sulphur;

R' is hydrogen, lower alkyl, carboxylic acid ester, carboxylic acid, carboxylic acid amide, or lower alkoxy;

X represents a covalent bond or a covalent chemical bridge consisting essentially of covalently linked lower alkylene groups, phenyl groups, substituted phenyl groups, oxygen atoms, sulphur atoms, or nitrogen atoms, alone or linked as ester amide, carbonate, carbamate, or ureido linkages; or combinations of said groups and linkages;

and A is a photosensitive anthracene radical or N-hetero-anthracene radical, which is unsubstituted or substituted with one or more lower alkyl radicals, cycloalkyl radicals or halogen (except iodine).

7. The polymeric material of claim 6 wherein the anthracene radical is linked to the polymer chain side group through its 9-position, and is substituted at its 10-position with a lower alkyl group R, so that the photoresponsive group corresponds to the general formula

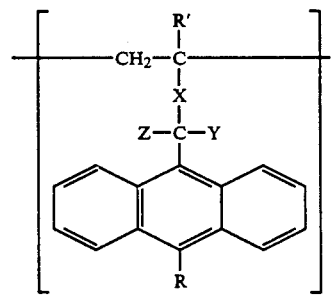

wherein X, Y, Z and R' have the meanings given in claim 6.

8. The polymeric material of claim 6 wherein group Y in formula I represents a lower alkyl group, and groups X and Z together form a heterocyclic group linked to the polymer through an alkylene, ester, amide, or ether group.

9. The polymeric material of claim 8 wherein the heterocyclic group is a cyclic ketal, or structure

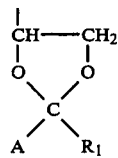

where $R_1$ represents a lower alkyl group or hydrogen, and A represents the sensitizer radical.

10. The polymeric material of claim 8 wherein the heterocyclic group is a cyclic hemi-thioketal or hemi-aminoketal, of structure

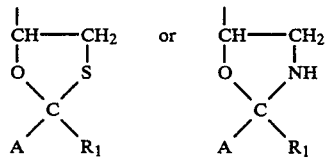

where $R_1$ represents a lower alkyl group or hydrogen, and A represents the sensitizer radical.

11. Polymeric materials containing photosensitive anthracene groups and comprising an ether-soluble but alcohol insoluble polymeric material, said anthracene groups being linked to the polymer backbone through a tetrahedral carbon atom at a position α to the anthracene moiety and a covalently linked chemical bridging group extending from the α-carbon to the polymer chain, said α-carbon-chemical bridging group resulting from the reaction of an aldehyde group on the anthracene with an aldehyde reactable group on a side group linked to the polymer backbone.

12. Polymeric materials according to claim 11 wherein said aldehyde reactable group is cyclic ketal, cyclic thioketal; cyclic thioketal; 1,2-diol; 1,3-diol; 1,2-aminoalcohol: 1,3-aminoalcohol; 1,2-dithiol; 1,2-aminothiol or orthoester.

13. A process for preparing polymeric photocatalysts according to claim 1, which comprises preparing a special monomer containing the sensitizer radical covalently bonded therein and also containing a polymerizable functionality, and copolymerizing said special monomer in appropriate proportions with a monomer copolymerizable therewith, to form a medium to high molecular weight copolymer containing said sensitizer radicals.

14. A process for preparing polymeric photocatalysts according to claim 1, which comprises grafting the sensitizer sub-units onto preformed medium to high molecular weight polymer.

15. A process for preparing polymeric photocatalysts according to claim 1, which comprises copolymerizing a special monomeric material containing a polymerizable group and a second functional group with a predominant monomer to form a medium to high molecular weight copolymer thereof, and subsequently covalently linkinq sensitizer sub-units to said second functional groups on the copolymer.

16. The process of claim 15 wherein said second functional group is protected during polymerization, and deprotected prior to reaction with said sensitizer sub-units.

* * * * *